(12) United States Patent
Longenecker et al.

(10) Patent No.: US 6,326,009 B1
(45) Date of Patent: *Dec. 4, 2001

(54) ENHANCEMENT OF THE CELLULAR IMMUNE RESPONSE

(75) Inventors: B. Michael Longenecker; Carina Henningsson, both of Edmonton (CA)

(73) Assignee: Biomira, Inc., Edmonton (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/022,025

(22) Filed: Feb. 11, 1998

Related U.S. Application Data

(63) Continuation of application No. 08/394,431, filed on Feb. 24, 1995, now Pat. No. 5,798,090, which is a continuation of application No. 07/883,234, filed on May 7, 1992, now abandoned, which is a continuation of application No. 07/524,310, filed on May 17, 1990, now abandoned, which is a division of application No. 07/222,390, filed on Jul. 21, 1988, now Pat. No. 4,971,795, which is a continuation of application No. 06/883,266, filed on Jul. 8, 1986, now abandoned.

(51) Int. Cl.$^7$ ..................................................... A61K 45/00

(52) U.S. Cl. ............................... 424/279.1; 424/184.1; 424/185.1; 424/186.1; 424/190.1; 424/93.71; 530/395

(58) Field of Search ........................... 424/184.1, 279.1, 424/93.71, 185.1, 186.1, 190.1; 530/395

(56) References Cited

U.S. PATENT DOCUMENTS

| | | | |
|---|---|---|---|
| 4,180,627 | * 12/1979 | Klesius et al. | 424/95 |
| 4,690,915 | * 9/1987 | Rosenberg | 424/93 |
| 4,971,795 | * 11/1990 | Longenecker et al. | 424/93 |

FOREIGN PATENT DOCUMENTS

| | | | |
|---|---|---|---|
| 2106935 | * 4/1983 | (GB) | C12N/5/00 |

OTHER PUBLICATIONS

Henningsson, et al., Induction of Immunity to a Mammary Adenocarcinoma using Purified shed Cancer Antigen and Synthetic Carbohydrates, Journal of Leukocyte Biology, vol. 38, abstract No. 70, Jul. 1985.

Henningsson, et al., Induction of Immunity to a Mammary Adenocarcinoma using Purified Shed Cancer Antigen and Synthetic Carbohydrate Tumor Associated Antigens, 5th Ann. Heritage Med. Res. Days, p. 52, Abstract No. 130, Nov. 21, and 22, 1985.

Henningsson, et al., Induction of Immunity to a Mammary Adenocarcinoma using Purified Shed Cancer Antigen and Snythetic carbohydrates, 6th Int. Congress of Immunology, Jul., 1986.

Codington, JF et al., "Further Studies on the Relationship Between Large Glycoprotein Molecules and Allotransplantability in the TA3 Tumor of the Mouse: Studies on Segregating TA3–Ha Hybrids", *J. Natl. Cancer Inst.* 6(4): 811–818 (Apr. 1978).

Codington, JF et al., "Cell Surface Characteristics of an Allotransplantable TA3 Ascites Subline Resulting from a Process of Immunoselection", *Cancer Research* 43:4373–4381 (Sep. 1983).

Friberg, S et al., "Comparison of an Immunoresistant and an Immunosusceptible Ascites Subline From Muring Tumor TA3. I. Transplantability, Morphology, and Some Physicochemical Characteristics", *J. Nat. Cancer Inst.* 48: 1463–1476 (1972).

Bretscher, PA, "In vitro induction of delayed–type hypersensitivity", *Eur. J. Immunol.* 9:311–316 (1979).

Klein, ed., Immunology: The Science of Self–Nonself Discrimination 465 (1982).

Goldstein, et al., J. Exp. Med., 162:1381 (1985).

Myrvik, et al., Fundamentals of Immunology 135–41 (1984).

Moreno, "Carbohydrates as Immunogens and Tolerogens: Antibody versus Cell–Mediated Immune Responses", in *Towards Better Carbohydrates Vaccines,* Chapter 19 (1987) at pp. 263, 267.

Springer, et al, 1984, "T and Tn General . . . " Science 224: 1198–1206.*

Bianchi, et al, 1981, "Clones of T cells mediate antigen–specific . . . " Nature 290 62–63.*

Leung, et al, 1980, "Specificity, Ly phenotype and H–2 . . . " J. Exp. Med 151:815–826.*

Greene, et al, 1984, "Delayed Hypersensitivity" In Fundamental Immunology, W.E. Paul Ed p. 685–696.*

Ertl, Cell Immunol, 62, 38–49, (1981).*

Benjamini et al, Chapter 15 in Basic and Clinical Immunology, Stites et al eds, 1984 (5$^{th}$ Edition), Los Altos, CA.*

Lefford, *Immunology,* 41, 635, (1980).*

Chemical Abstracts, 78, 27836Z (for Cooper, Scand. J. Immunol., 1(3), 237–45).*

Havelle et al, J. Immunol, 137(5), 1448–54, 1986.*

Miller, et al. 1982 "Further Studies on the relationship between . . . " J. N. C. I. 68(6): 981–985.*

* cited by examiner

Primary Examiner—Jeffrey Stucker
(74) Attorney, Agent, or Firm—Iver P. Cooper

(57) ABSTRACT

DTH-Effector cells are primed with carbohydrate antigens and used to enhance the cellular immune response. Tumors have been inhibited by DTH-Effector cells primed with epiglycanin and with synthetic T and Tn antigens. Either the DTH-Effector cells, or these tumor-associated carbohydrate antigens directly, may be used for tumor prophylaxis and therapy.

61 Claims, 8 Drawing Sheets

ENHANCEMENT OF THE CELLULAR IMMUNE RESPONSE

This is a continuation of parent application Ser. No. 08/394,431 filed Feb. 24, 1995, U.S. Pat. No. 5,798,090, which is a continuation of Ser. No. 07/883,234 filed May 7, 1992, now abandoned, which is a continuation of Ser. No. 07/524,310 filed May 17, 1990, now abandoned, which is a division of Ser. No. 07/222,390 filed Jul. 21, 1988, now U.S. Pat. No. 4,971,795, which is a continuation of Ser. No. 06/883,266 filed Jul. 8, 1986, now abandoned.

BACKGROUND OF THE INVENTION

Vertebrates have two basic immune responses: humoral or cellular. Humoral immunity is provided by the special class of cells produced by B lymphocytes. These cells produce antibodies which circulate in the blood and lymphatic fluid. On the other hand, cell mediated immunity is provided by the T cells of the lymphatic system.

The cellular immune response is particularly effective against fungi, parasites, intracellular viral infections, cancer cells and foreign matter, whereas the humoral response primarily defends against the extracellular phases of bacterial and viral infections.

Containment of antigen at its point of entry is accomplished by walling off the area by local inflammation. Acute inflammation is characterized by the influx of plasma proteins and polymorphonuclear leukocytes. Chronic inflammation is characterized by the infiltration of T-lymphocytes and macrophages. When acute (antibody induced) and chronic (T-cell induced) inflammations occur in the skin, they are called immediate and delayed type hypersensitivity reactions respectively. ITH peaks at 24 hours, and subsides in 48 hours DTH appears in 24–48 hours and peaks at 48–72 hours. The subset of T cells involved in DTH reactions are called here DTH-Effector cells.

Epiglycanin (epi) is the major cell surface glycoprotein produced by the mammary adenocarcinoma transplantable cell line TA3Ha. Friberg, Jr., J.N.C.I., 48:1463 (1972); Codington, et al., Canc. Res., 43:4373 (1983). The TA3Ha carcinoma cells are covered by a mucin-like glycocalix composed mainly of epiglycanin. Codington, et al., J.N.C.I., 60:811 (1978); Miller, et al., J.N.C.I., 68:981 (1982). Epi is mainly carbohydrate in composition, and expresses multiple T and Tn determinants. T and Tn are general carcinoma autoantigens. Springer, Science, 224:1198 (1984).

Synthetic T and Tn antigens have been prepared, and used in DTH diagnostics. Lemieux, Ep Appl. 44,188. However, their therapeutic or prophylactic use has not been disclosed.

Bretscher, Eur. J. Immunol., 9:311–316 (1979) cultured DTH-Effector cells in vitro and injected them with the sensitizing antigen (burro erythrocytes) into the foot pads of mice. We have used cancer-associated, well characterized carbohydrate antigens to sensitize effector cells and have taught a therapeutic use for them.

It is known that tumors may be treated with a mixture of IL-2 and IL-2-activated killer cells. See Fortune, 16–21 (Nov. 25, 1985), reporting on the work of Steven Rosenberg. The IL-2 induces a general immune response. It thus places a heavy burden on the immune system, diverting resources from the desired cellular response. High, possibly toxic levels of IL-2 are required to induce a cellular response. At these levels, it may unintentionally induce an autoimmune response. Our procedure induces a response which is specific, because the cells recognize a cancer-associated carbohydrate marker only a low level of our inducer is required to stimulate the cellular immune system.

SUMMARY OF THE INVENTION

We have found that the cell-mediated immune response to cancer cells is enhanced by parenteral administration of natural and synthetic cancer-associated carbohydrate antigens or by parenteral administration of DTH effector cells primed by such antigens. This enhancement is likely to be advantageous for both therapy and prophylaxis when the body's primary defense against a challenge is a cellular immune response, e.g., against tumors. The use of other specific carbohydrate antigens, including polysaccharides, glycolipids and glycoproteins, may be useful in protecting a subject against other threats controlled by T cells. It is known that parasites, viruses, bacteria and fungi bear surface carbohydrate determinants.

While we do not favor the use of lymphokines (e.g., IL-2) alone to induce a general cellular immune response, lymphokines may be used in conjunction with the specific antigens or primed DTH-Effector cells of this invention to enhance the specific CMI response.

DETAILED DESCRIPTION OF THE INVENTION

Example 1

Figure 1:
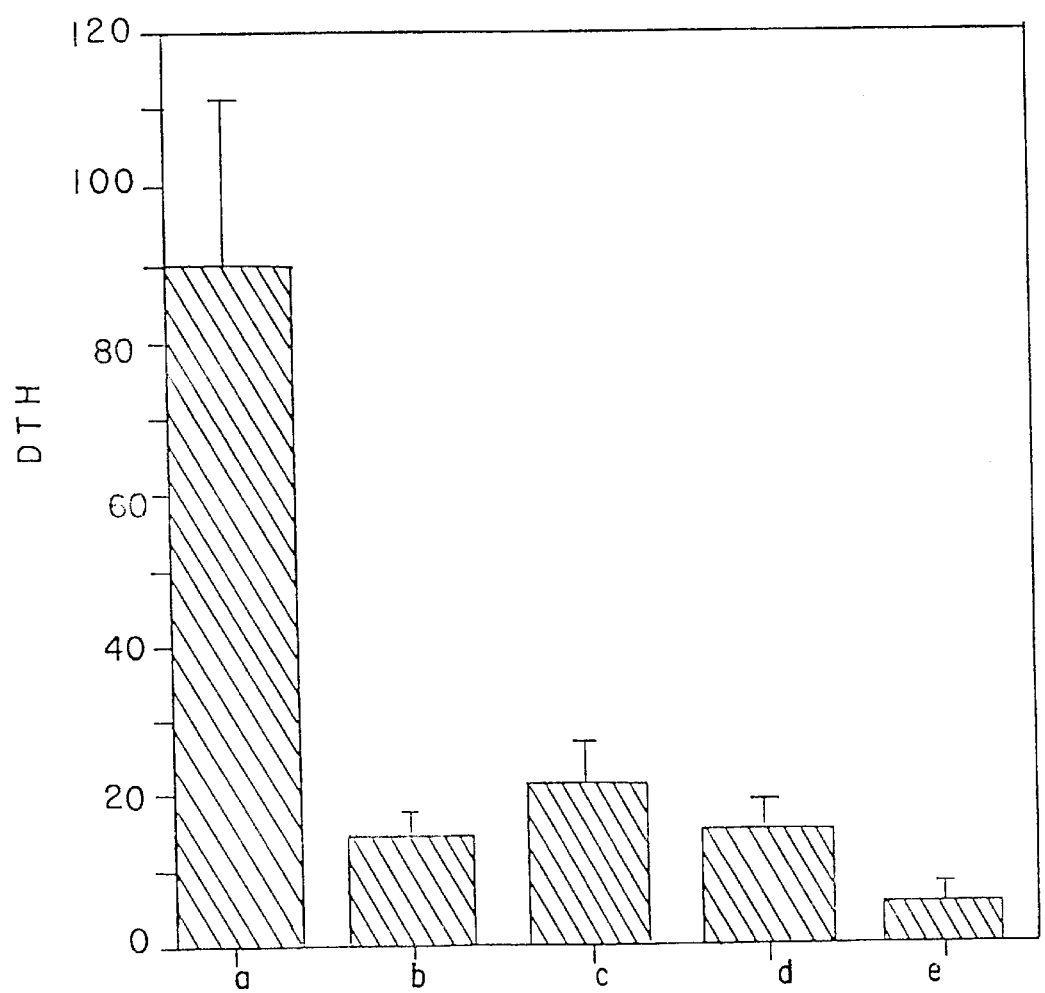
FIG. 1 shows that epi-primed splenocytes induce local DTH swellings in the presence of epi, while unprimed spleen cells, irradiated tumor cells, and primed cells in the absence of antigen do not.

Use of S-TAGS to Enhance Cellular Immune Response to Tumors

Synthetic tumor-associated glycoproteins (S-Tags) and other carbohydrate antigens are known in the art and may be prepared by any convenient technique. T and Tn antigens are preferred. For synthetic methods, see Kaifu and Osawa, Carbohydr. Res., 58:235 (1977); Ratcliffe, et al., 93:35 (1981); Paulsen, et al., 104:195 (1982); Bencomo and Sinay, 116:69 (1983).

Soluble S-Tags or their aggregates are mixed with an adjuvant for intradermal, intravenous, intramuscular or intraperitoneal administration.

Groups of five mice at a time were primed with specific doses of T-alpha (TF), T-beta (asialo-GM1 disaccharide) and Tn S-Tags. After 2–3 days, they were challenged with $3 \times 10^3$ live TA3Ha cells. Markedly increased survival was noted in mice receiving about 1 ug of synthetic antigen. Thus, for T-beta, the following results were observed (Table I):

TABLE I

| Dose | Survival (days) |
| --- | --- |
| 0.2 ug | 20, 27, 27, 29, 31 |
| 1.0 ug | 27, 38, 43, 43, 49 |
| 2.0 ug | 16, 21, 24, 30 |
| 10 ug | 20, 21, 28, 33 |
| 20 ug | 21, 21, 28, 28 |
| 50 ug | 16, 18, 31 |
| 100 ug | 20, 20, 21, 27, 29 |
| PBS | 23, 27, 29 |
| Norm | 13, 13, 18, 27, 28 |

It should be noted that TA3Ha is very deadly. The normal post-transplantation life expectancy of a mouse is only 15–20 days.

Example 2

Use of Cultured DTH Effector Cells as Tumor Inhibitors

We obtained mouse primed DTH effector cells by the following procedure. CAF1/J (BalbxA/J) mice from our animal unit were immunized with 30 ug Epi (or 2 ug of any synthetic antigen), in 50% complete Freund's adjuvant, intraperitoneally, boosted one week later with a similar injection. 7–10 days after the last injection the animals were sacrificed, their spleens removed and passed through a nylon mesh to make a single cell suspension. The cells were washed and cultured in a costar well at $1.5 \times 10^7$ cells/8 ml. (RPMI+P.S.+10% FCS)/well. Each well received 10 ug epi (or 1–2 ug of any of the synthetic antigens). The cells were cultured at 37° C. and 5% $CO_2$ for 6 days and then harvested by gently dissociating them from the plastic with a rubber policeman. The primed cells were then tested for DTH reactivity with a number of antigens, and for their ability to inhibit the growth of TA3Ha cell line in vivo.

To obtain human primed DTH Effector cells, we would use a modification of the method of Rosenberg. Lymphocytes are removed from blood of a living subject by plasmapheresis. The lymphocytes are cultured with a specific antigen, such as cancer-associated glycoprotein (epiglycanin or a T or Tn S-TAG). We prefer use of these more specific primers to the lymphokine (IL-2) used by Rosenberg, to avoid an autoimmune reaction by the IL-2 stimulated DTH-Effector cells upon injection into the subject. The human lymphocytes are cultured in suitable media for 6 days at a preferred concentration of about $10^6$ cells/ml. The cells are washed to remove antigen. The cells may then be returned to the patient, intravenously, for therapeutic or prophylactic purposes.

We have demonstrated that co-injection of a mammal with epigycanin-primed DTH Effector cells and antigen (irradiated tumor cells) induced a DTH reaction (FIG. 1). Spleen cells from mice primed and boosted with 30 ug and 20 ug of epi extracted and purified from TA3Ha ascites fluid and CFA (intraperitoneally administered one and two weeks beforehand) were cultured at $1.5 \times 10^7$ cells/well with: (a) 10 ug epi/well and (b) no antigen. In addition, unprimed spleen cells were cultured with (c) 10 ug epi/well and (d) no antigen. Cultures were harvested on the 6th day and $10^7$ cells were injected subcutaneously into the foot pad of unimmunized mice together with $10^6$ irradiated TA3Ha cells. As a control (e), $10^6$ irradiated TA3Ha cells were injected alone. All the DTH values are presented as net DTH swellings, i.e., [swelling of primed cells +Ag.]–[swelling of primed cells alone]. The large differential responses demonstrated that immunization with a cancer mucin can induce a DTH reaction to those cancer cells which have the mucin at the cell surface.

Figure 2:
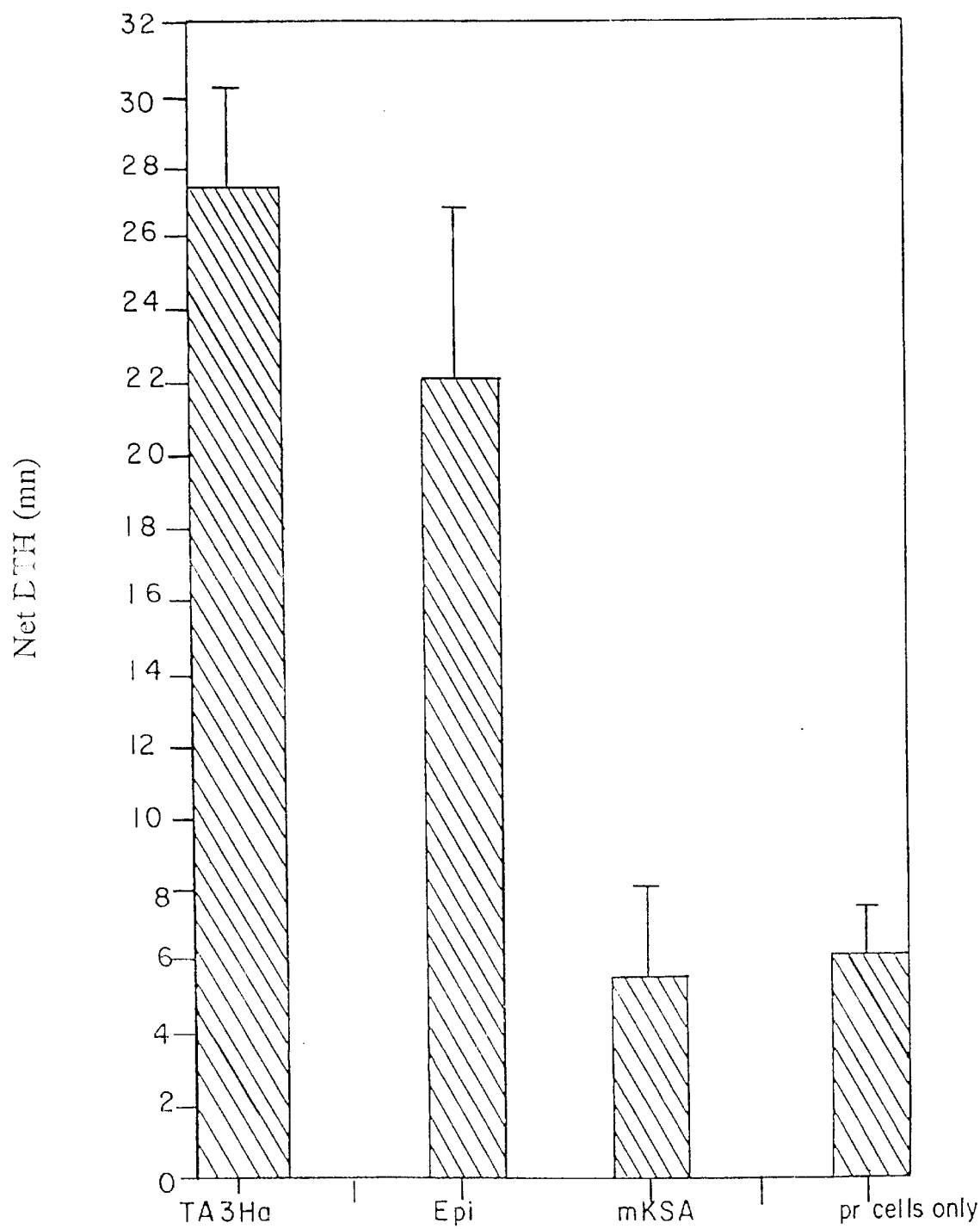
FIG. 2 shows that this reaction is specific to cancer cell lines bearing the primer as a surface antigen.

Subsequently, we showed that this reaction was tumor-specific (FIG. 2). A DTH effector cell population was generated as in Example I and tested with a) TA3Ha; b) Epi-M (epi linked to a sepharose microsphere); c) mKSA; and d) no antigen. All the DTH values are presented as net DTH swellings, i.e., [swelling of primed cells+Ag.]–[swelling of primed cells alone]. The results was that the immunization with the epi mucin induced a specific DTH response to the mucin and to the cells which bear the mucin (TA3Ha) but not against those that do not bear the mucin (mKSA).

Figure 3:
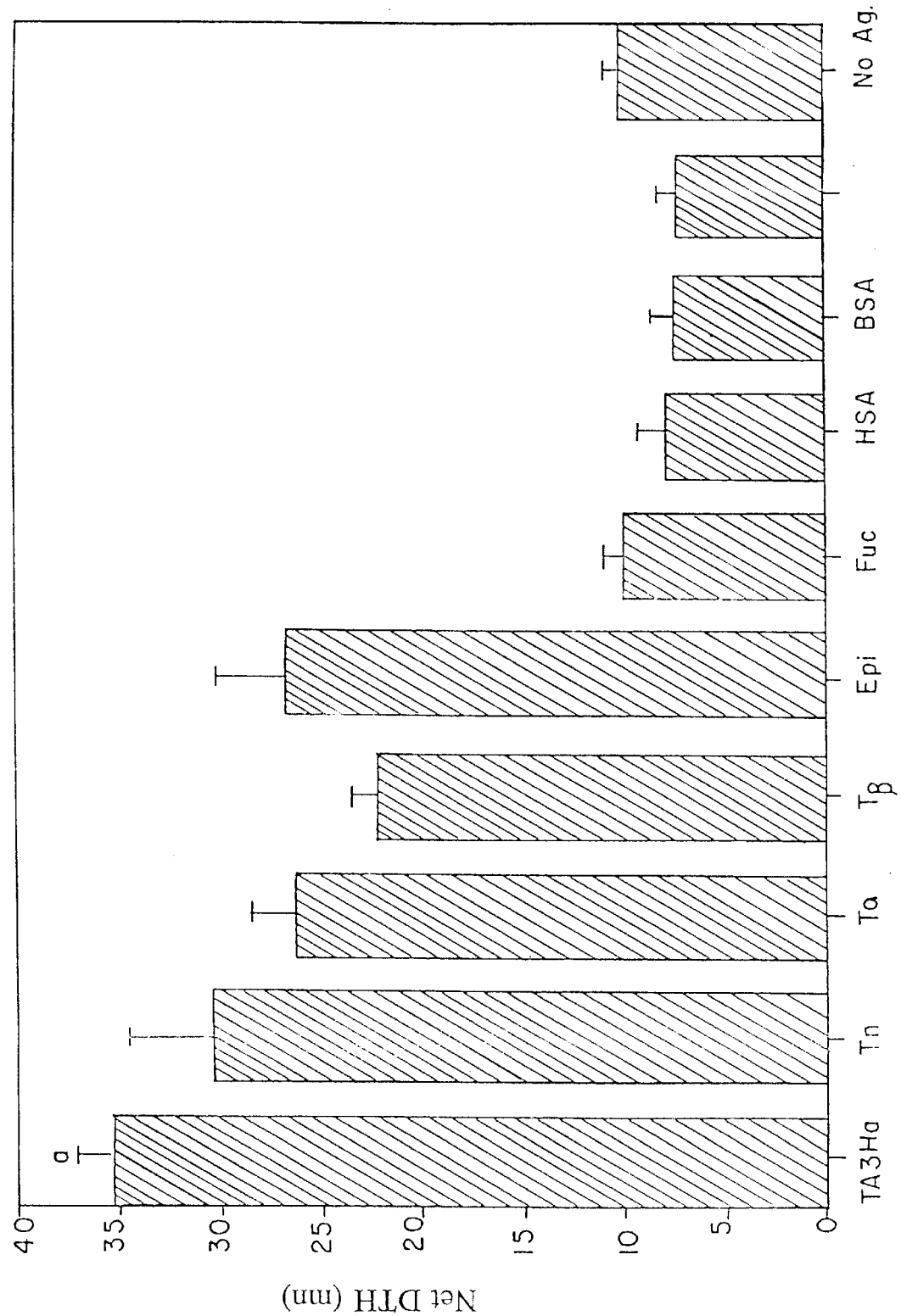
FIG. 3 shows that the reaction was with the T alpha, T beta and Tn determinants of epi.

We also explored the antigenic specificity of the DTH reaction in greater detail (FIG. 3). $10^7$ T cells were primed with epi and were co-injected with a series of antigens (TA3Ha, Tn, T-alpha, T-beta, Epi, Fucose ("Fuc"), HSA, BSA, sepharose microspheres, and no antigen). All soluble antigens were linked to sepharose microspheres and used at 12 ug/foot pad except epi which was used at 50 ug/foot pad. All DTH results are net DTH measurements. The experiment shows that the DTH measured by the injection of epi reacts with the carbohydrate determinants on S-Tags which are also know to be epi determinants but not those carbohydrates determinants not represented on epi. (eg. Fucose).

SUMMARY OF SPECIFICITY OF DTH RESPONSE

| IMMUNIZING Ag: | TRIGGERING Ag: | | | | | |
| --- | --- | --- | --- | --- | --- | --- |
| | Epi | Tn | Ta | Tb | Fuc | BSA |
| Epi: | + | + | + | + | – | – |
| $T_a$: | + | + | + | + | – | – |
| $T_B$: | + | + | + | + | – | – |
| Tn: | + | + | + | + | – | – |
| None: | – | – | ND | ND | ND | |

Figure 4:
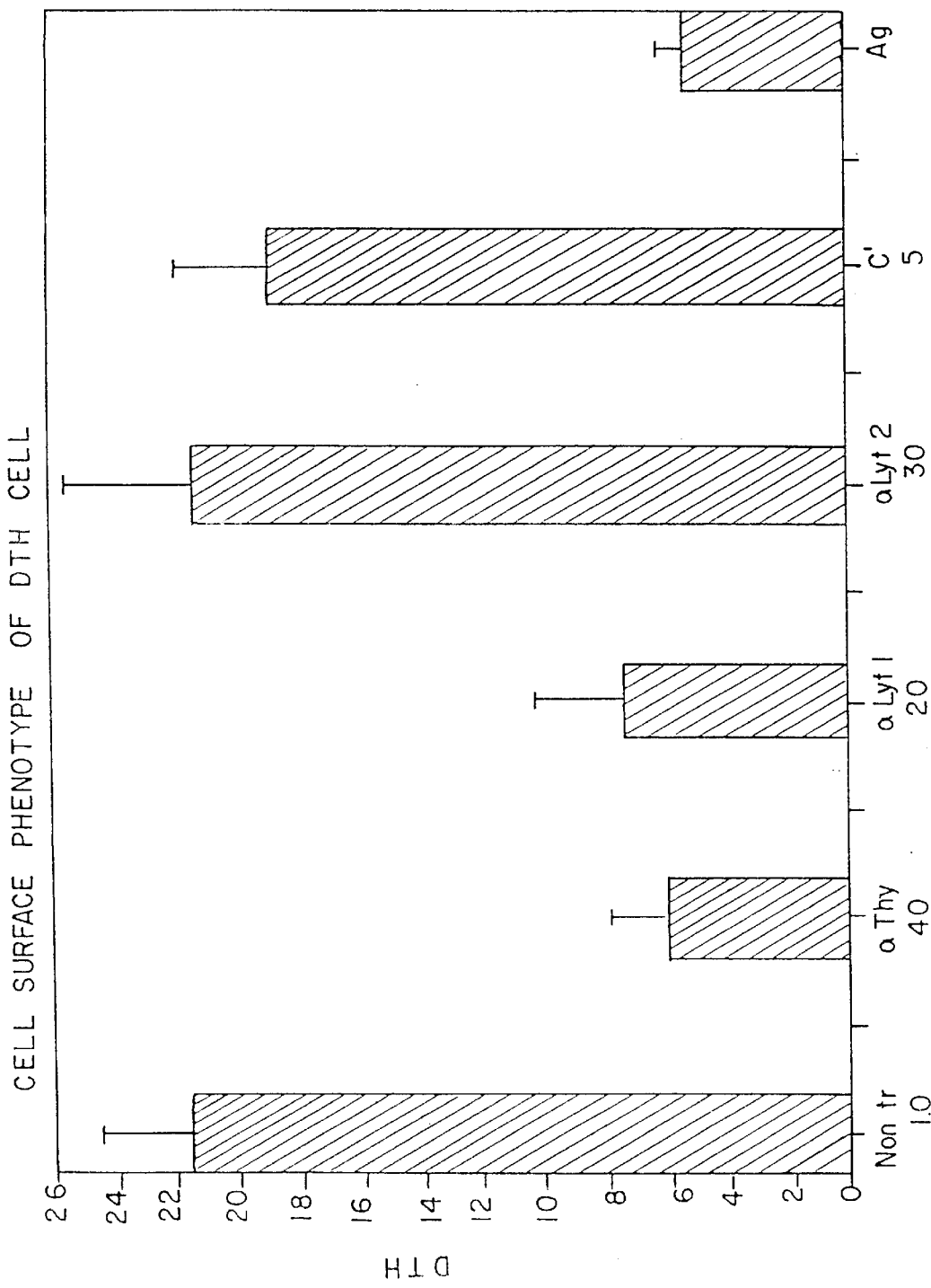
FIG. 4 shows that the phenotype of the anti-carbohydrate DTH effector cells is Thy-1+, Lyt-1+, Lyt-2−.

To confirm that the reactions we were witnessing were indeed DTH reactions we designed an experiment to check for the cell surface phenotype of DTH effector cells. (FIG. 4) An effector cell population was prepared as before and treated with a) no treatment; b) anti-Thy 1.2 antibodies plus complement; c) anti-Lyt 1.2 plus complement; d) anti-Lyt 2.2 plus complement; and e) complement alone. The antigen alone was also used as a control. All the values presented are net DTH. Treatment of the DTH effector cells with anti-Thy or anti-Lyt-1 antibodies with complement kills the DTH effector cells but treatment with anti-Lyt-2 plus complement did not kill the DTH effector cells; thus, the phenotype of the specific anti-carbohydrate DTH effector cells is Thy-1+, Lyt-1+, Lyt-2[31]—the phenotypic pattern shown by other DTH effector cells reacting against proteins. See Fujiwara, J. Immunol, 135:2187 (September 1985).

The protocol for this comparison was as follows. A primed cell population was obtained, washed, counted, and divided into separate tubes for treatment. The cells were gently pelleted and resuspended in Leibowitz media containing 1) anti Thy 1.2 antibody (at 1/1000 diln., obtained from NEN), 2) anti Lyt 1.2 antibody (at 1/1000 diln., obtained from NEN) or 3) anti Lyt 2.2 antibody (at 1/1000 diln., obtained from NEN) at $2 \times 10^7$ cells/ml., and incubated at 4° C. for 45 min. The cells were then spun down and resuspended in guinea pig complement (1/10 diln.) in Leibowitz media at $2 \times 10^7$ cells/ml., and incubated for 30 min. in a 37° C. water bath. After incubation, cells were washed with Leib+10% FCS and counted.

A comparative study was undertaken to determine whether the reaction was of the delayed type. DTH Effector cells were injected together with TA3Ha and the reaction was compared with reactions in other mice injected with only the DTH Effector Cells or only the TA3Ha. It was found that the reaction peeked in 48 hours and had disappeared by 96 hours. No DTH (emphasis on delayed) was found with the other two immunogens.

As further confirmation that the reaction observed was a DTH, a mononuclear infiltrate was observed the site of swelling.

The foregoing experiments all related to local transfer of DTH. We also investigated the possibility that DTH Effector cells would have a systemic effect.

Figure 5:
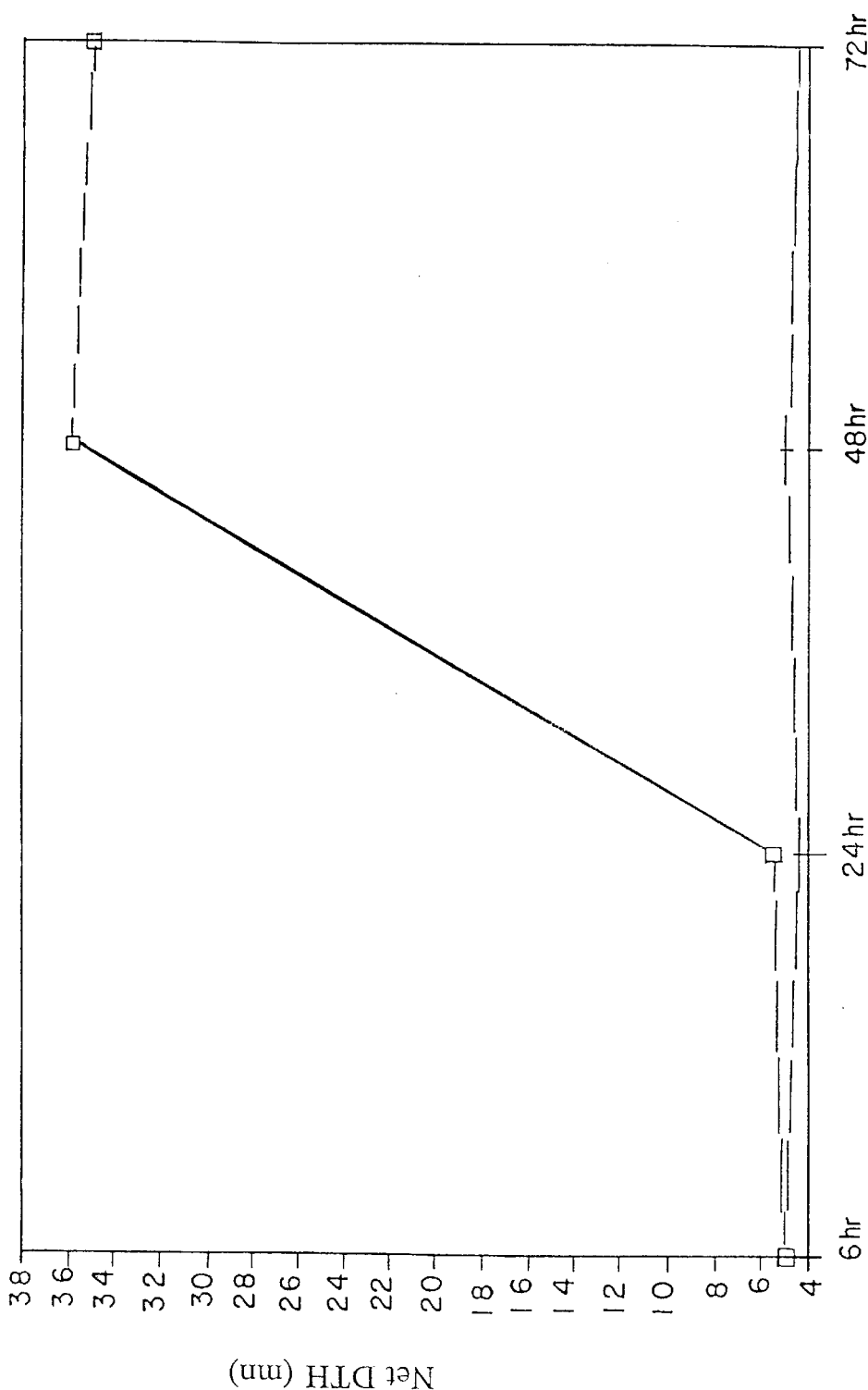
FIG. 5 shows systemic transfer of DTH by a DTH reaction to irradiated tumor cells after IV administration of Effectors.

DTH effector cells were administered intravenously to the host animal. Four hours later, irradiated TA3Ha cells were injected into the footpad. At 6, 24, 48 and 72 hours, the DTH reaction was measured (open boxes) and compared with a negative control (plusses) (FIG. 5).

The irradiated tumor cells used in the above-described experiments will not proliferate. In the next experiments, however, untreated tumor cells were employed.

DTH primed cells were induced as described above. $5 \times 10^7$ primed cells plus $5 \times 10^5$ live tumor cells were injected s.c. into the foot pad. The control mice were injected with normal spleen cells plus tumour cells. The foot pad swelling was typically measured at 12, 24, 48, and 72 hours and every two days thereafter. The determine the component of the swelling which was due to a DTH reaction, as opposed to a combination of DTH and tumour growth, mice were injected with primed or normal cells plus irradiated tumor cells. The swelling was attributed only to the DTH reaction. Tumor growth was measured every 2 days starting 48 hours after the peak DTH swelling. The DTH and the tumor size were measured using calipers in order to estimate the increase in foot pad thickness.

Figure 6:
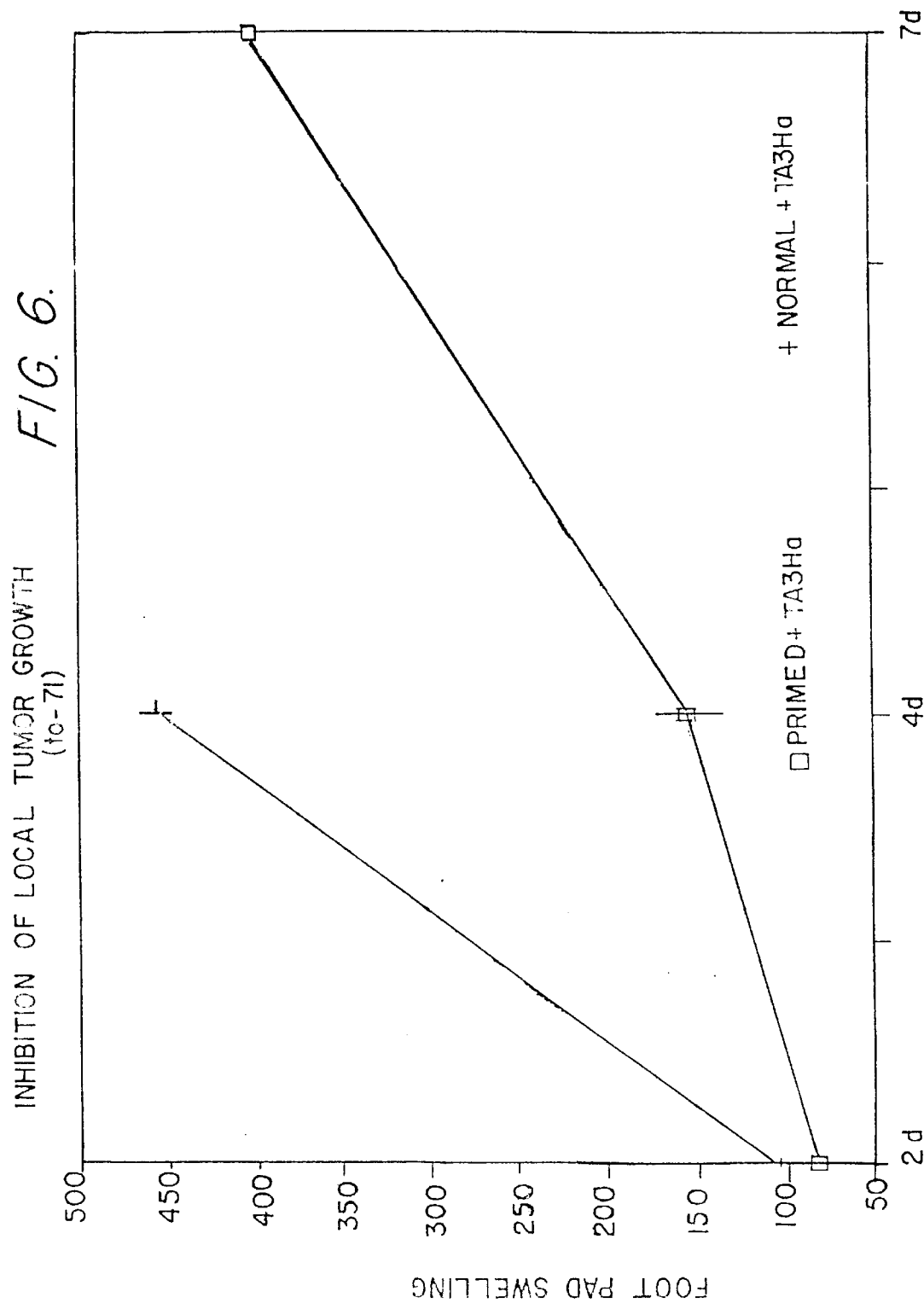
FIG. 6 shows inhibition of tumor growth after local transfer of DTH-Effector cells mixed with tumor cells.

FIG. 6 shows that the primed cells inhibited the growth of the TA3Ha tumor.

Other experiments have shown that the nature of the reaction to the antigen is dependent on the dose of primer administered to the DTH-Effector cells. At lower doses, cell-mediated immunity was predominant, while at higher doses, the reverse was true.

Figure 7:
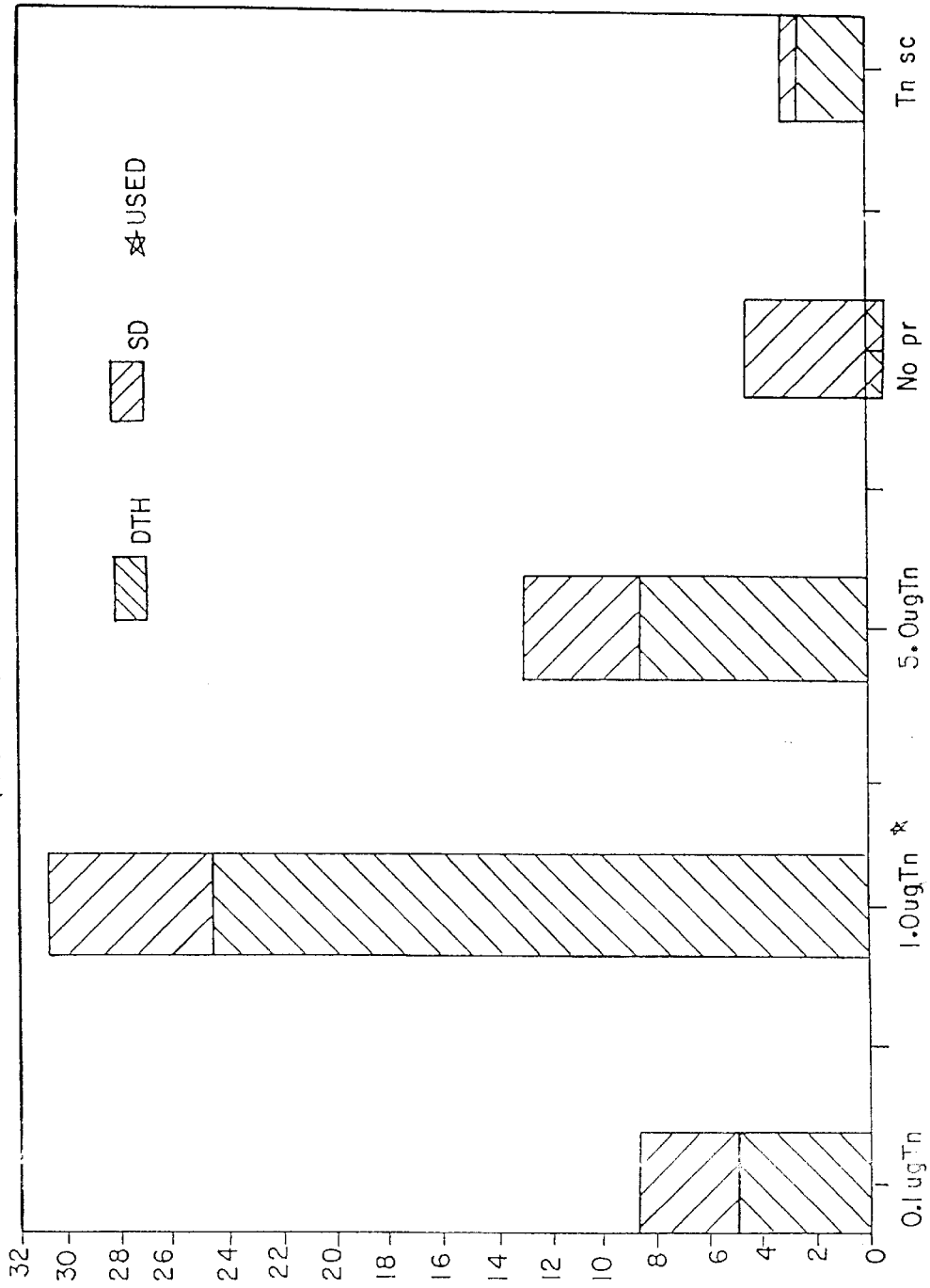
FIG. 7 shows the importance of the priming dose.

A dose dependence was also found when splenocytes are primed with Tn in culture (FIG. 7).

We have further shown that the DTH effector cells stimulated by epi will "home in" on a tumor and inhibit tumor growth. DTH-Effector cells were primed with epi as previously described. One day prior to intravenous injection of the epi-primed DTH effector cells, the TA3Ha tumor was transplanted into the footpads of mice. Mice with tumors transplanted at the same time were used as controls and tumor growth as determined by measuring the swelling of the footpads (in mm) with calipers. The size of the footpad of each mouse at the times stated is given in the tables below:

| EXPERIMENT 1 | | |
|---|---|---|
| | Day 6, post iv | Day 8, post iv |
| Systemic Transfer Effector cells | 10, 12, 12, 10, 15 | 50, 15, 80, 60, 50 |
| Control Animals (3 mice) | 140, 25, 35 | 190, 200, 220 |

| EXPERIMENT 2 | | | | |
|---|---|---|---|---|
| | Day 5 post iv | Day 6 post iv | Day 8 post iv | Day 10 post iv |
| Systemic Transfer Effector cells (4 mice) | 10,20,15,10 | 55,20,15,20 | 100,140,80,60 | 300,360,340, 380 |
| Control Animals (4 mice) | 60,75,60,110 | 170,160,170 110 | 340,300,320, 340 | greater than 500 (3 mice), 4 |

As may be seen from the above data, the IV-administered, epi-primed DTH-Effector cells exerted a tumor-inhibitory effect at the footpad site of tumor transplantation.

Example 3

Use of Epiglycanin as a Tumor Inhibitor

Epiglycanin (epi) was extracted from the ascites fluid of TA3Ha tumor-bearing mice.

Ascites from outbred TA3Ha ip tumors was collected and cells were removed by centrifugation. The samples were stored frozen. Before extraction, the ascites was thawed and incubated at 37° C. for 2 hours, and any aggregates were removed by centrifugation. The freezing, thawing and clotting procedure was performed twice before PNA extraction.

25–40 ml. bed volume of PNA agarose (E. Y. Laboratories) was washed with PBS, mixed with ascites and tumbled gently at 4° C. for 24–48 hours. The slurry was poured into a column and extensively washed with PBS at 4° C. with continuous stirring for 24 hours. Epi was eluted from PNA agarose using galactose. The eluted epi-galactose mixture was then dialyzed against PBS to remove the galactose. The sample was lyophilized and stored at −20° C. in dessicator.

Groups of five mice at a time were primed with specific doses of epi. After 2–3 days they were challenged with $3 \times 10^3$ live TA3Ha cells. Table 2 below shows the relationship between the priming dose and survival.

TABLE 2

| Priming dose: | Survival: (days) | ave. | s.e. | No. alive (at d. so) |
|---|---|---|---|---|
| 0.2 ug | 19, 25, 27, 49,49 | 33.8 | 6.3 | 2/5 |
| 1 ug | 25. 49,49,49,49 | 44.2 | 4.8 | 4/5 |
| 2 ug | 14, 19, 19, 25, 49 | 25.2 | 6.2 | 4/5 |
| 10 ug | 20, 22, 22, 25 | 22.3 | .9 | 0/4 |
| 20 ug | 20, 22, 25, 49, | 29.0 | 6.0 | 1/5 |
| 100 ug | 19, 19, 20, 25, 49 | 25.5 | 5.3 | 1/5 |
| PBS | 19, 19, 20, 20 | 20 | 0.3 | 0/4 |

Data calculated on day 49 i.e. these mice are still alive. These mice were sacrificed on day 88 to continue the experiment.

Thus, the preferred priming dose was 1 ug, and this dosage appeared to confer protective immunity against TA3Ha cells.

Figure 8:
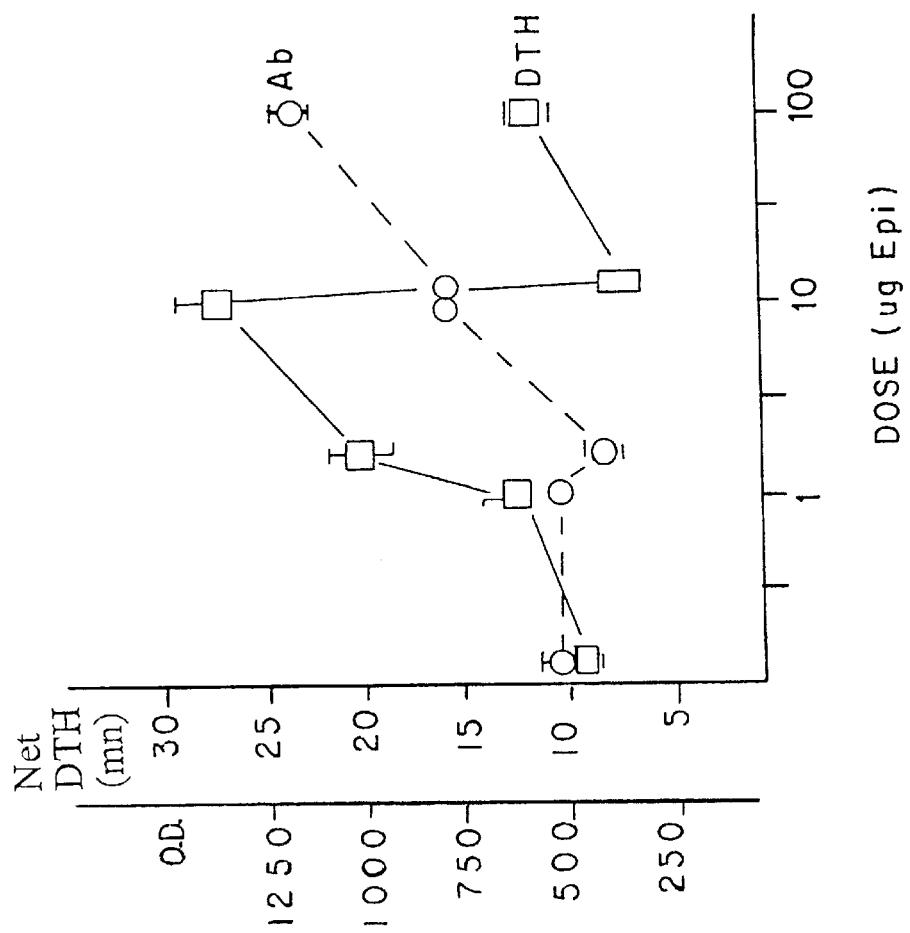
FIG. 8 shows that at lower doses of antigen the cellular response predominated.

In another experiment, it was determined that the humoral response was negligible at that dosage (FIG. 8), suggesting that the tumor was inhibited by a T cell-mediated mechanism.

A summary of our experiences with Epi and T-alpha in tumor inhibition is given in Table 3 below:

TABLE 3

In Vivo Protection;
Number of animals alive at 4 weeks.

| Dose of Ag | Epi | Ta | Glu-BSA/HSA |
|---|---|---|---|
| 0.1 ug | 1/20 | 4/15 | 0/10 |
| 0/5 ug | 5/20 | 7/15 | 0/10 |
| 1.0 ug | 8/20 | 5/15 | 0/10 |
| 5.0 ug | 8/15 | 6/15 | 0/10 |
| 10.0 ug | 7/20 | 3/15 | 0/10 |
| cont. | 0/20 | 0/15 | 0/10 |

Since Glu-BAS/HSA presents a carbohydrate which in not expressed on the surface of the TA3Ha tumor cells, administration of that substance did not provide protection. Epi, which is the predominant surface carbohydrate antigen on TA3Ha cells, and T-alpha, which is one of the Epi determinants, did provide protection.

What is claimed is:

1. A method of enhancing cellular immunity in a mammal which comprises administering to the mammal an immunologically effective amount of a carbohydrate antigenic determinant bearing antigen, said antigen being a synthetic conjugate comprising a carbohydrate antigenic determinant and an immunogenic carrier not naturally conjugated with said determinant, said mammal subsequently exhibiting a cellular immune response elicited by said antigen and specific to the carbohydrate antigenic determinant of said antigen, where said antigen is parenterally administered.

2. The method of claim 1 where said antigen consists essentially of said determinant and said carrier.

3. The method of claim 2 in which said determinant is synthetic.

4. The method of claim 2 which consists essentially of administering said antigen.

5. The method of claim 4 in which said determinant is synthetic.

6. The method of claim 5 wherein the carbohydrate antigen is a mucin.

7. The method of claim 5 in which the determinant comprises the Tn structure.

8. The method of claim 5 in which the determinant comprises the T-alpha or T-beta structure..

9. The method of claim 5 in which the immunity is immunity to parasite and the determinant is parasite-associated.

10. The method of claim 5 in which the immunity is immunity to virus and the determinant is virus-associated.

11. The method of claim 5 in which the immunity is immunity to bacteria and the determinant is bacteria-associated.

12. The method of claim 5 in which the immunity is immunity to fungi and the determinant is fungi-associated.

13. The method of claim 5 in which the carrier is carbohydrate so that the antigen is a polysaccharide.

14. The method of claim 5 in which the carrier is lipid so that the antigen is a glycolipid.

15. The method of claim 5 where said antigen comprises a carbohydrate chain of epiglycanin.

16. The method of claim 5 in which the carbohydrate determinant is associated with a mammary adenocarcinoma.

17. The method of claim 5 where said antigen comprises a carbohydrate chain of a mucin.

18. The method of claim 17 in which the mucin is tumor-associated.

19. The method of claim 5, wherein an adjuvant is also administered.

20. The method of claim 19, wherein the response is mediated by the DTH effector cells of said mammal, said cells having a CD5 positive, CD8 negative phenotype.

21. The method of claim 20 in which the determinant is the Tn determinant.

22. The method of claim 20 in which mammal is a human being.

23. The method of claim 20 in which the carbohydrate determinant is associated with adenocarcinomas.

24. The method of claim 20 in which the carrier is a protein.

25. The method of claim 20 in which the determinant is a monosaccharide.

26. The method of claim 20 in which the determinant is a disaccharide.

27. The method of claim 20 in which the immunity is immunity to tumors and the determinant is tumor-associated.

28. The method of claim 27 in which the determinant is the T determinant.

29. The method of claim 27 in which amount of carbohydrate antigen is selected so that the cellular immune response predominates over the humoral immune response.

30. The method of claim 27 in which the tumor-associated determinant is naturally associated in tumors with a glycoprotein.

31. The method of claim 1 which consists essentially of administering said antigen.

32. The method of claim 31 in which said determinant is synthetic.

33. The method of claim 1 in which said determinant is synthetic.

34. The method of claim 1 where said antigen is administered intradermally, intravenously, intramuscularly, or intraperitoneally.

35. The method of claim 1, wherein an adjuvant is also administered.

36. The method of claim 1, wherein the response is mediated by the DTH effector cells of said mammal, said cells having a CD5 positive, CD8 negative phenotype.

37. The method of claim 1 in which the immunity is immunity to tumors and the determinant is tumor-associated.

38. The method of claim 37 wherein said carrier is not a tumor-associated antigen or a portion thereof.

39. The method of claim 1 in which the determinant is the Tn determinant.

40. The method of claim 1 in which the determinant is the T determinant.

41. The method of claim 1 in which the amount of carbohydrate antigen is selected so that the cellular immune response predominates over the humoral immune response.

42. The method of claim 1 in which the tumor-associated determinant is naturally associated in tumors with a glycoprotein.

43. The method of claim 1 in which the mammal is a human being.

44. The method of claim 1 in which the carbohydrate determinant is associated with adenocarcinomas.

45. The method of claim 1 in which the carrier is a protein.

46. The method of claim 1 wherein the carbohydrate antigen is a mucin.

47. The method of claim 1 in which the determinant comprises the Tn structure.

48. The method of claim 1 in which the determinant comprises the T-alpha or T-beta structure.

49. The method of claim 1 in which the determinant is a monosaccharide.

50. The method of claim 1 in which the determinant is a disaccharide.

51. The method of claim 1 in which the carrier is carbohydrate so that the antigen is a polysaccharide.

52. The method of claim 1 in which the carrier is lipid so that the antigen is a glycolipid.

53. The method of claim 1 where said antigen comprises a carbohydrate chain of epiglycanin.

54. The method of claim 1 in which the carbohydrate determinant is associated with a mammary adenocarcinoma.

55. The method of claim 1 where said antigen comprises a carbohydrate chain of a mucin.

56. The method of claim 1 in which the mucin is tumor-associated.

57. A method of enhancing cellular immunity in a mammal which comprises administering to the mammal an immunologically effective amount of a carbohydrate antigenic determinant bearing antigen, where said antigen is not a glycoprotein, said antigen being a synthetic conjugate comprising a carbohydrate antigenic determinant and an immunogenic carrier said mammal subsequently exhibiting a cellular immune response elicited by said antigen and specific to the carbohydrate antigenic determinant of said antigen, where said antigen is parenterally administered.

58. The method of claim 1 in which the immunity is immunity to parasites and the determinant is parasite-associated.

59. The method of claim 1 in which the immunity is immunity to virus and the determinant is virus-associated.

60. The method of claim 1 in which the immunity is immunity to bacteria and the determinant is bacteria-associated.

61. The method of claim 1 in which the immunity is immunity to fungi and the determinant is fungi-associated.

* * * * *